United States Patent
Jeon

(10) Patent No.: US 9,990,710 B2
(45) Date of Patent: Jun. 5, 2018

(54) APPARATUS AND METHOD FOR SUPPORTING COMPUTER AIDED DIAGNOSIS

(71) Applicant: SAMSUNG ELECTRONICS CO., LTD., Suwon-si (KR)

(72) Inventor: Joo Hyuk Jeon, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 262 days.

(21) Appl. No.: 14/860,905

(22) Filed: Sep. 22, 2015

(65) Prior Publication Data
US 2016/0093046 A1   Mar. 31, 2016

(30) Foreign Application Priority Data
Sep. 26, 2014   (KR) .................. 10-2014-0129559

(51) Int. Cl.
| G06K 9/00 | (2006.01) |
| G06T 7/00 | (2017.01) |
| G06F 19/00 | (2018.01) |
| G06T 7/20 | (2017.01) |

(52) U.S. Cl.
CPC ........ G06T 7/0012 (2013.01); G06F 19/3406 (2013.01); G06T 7/20 (2013.01); *G06T 2207/10132* (2013.01); *G06T 2207/20104* (2013.01)

(58) Field of Classification Search
CPC ............. G06T 7/0012; G06T 7/20; G06T 2207/10132; G06T 2207/20104; G06F 19/3406
See application file for complete search history.

(56) References Cited

U.S. PATENT DOCUMENTS

| 7,058,210 B2* | 6/2006 | Mundy | A61B 6/00 382/128 |
| 7,672,497 B2* | 3/2010 | Nicponski | G06T 7/0012 382/128 |
| 7,840,062 B2* | 11/2010 | Boroczky | G06K 9/3233 378/62 |

(Continued)

FOREIGN PATENT DOCUMENTS

EP   2 620 911 A1   7/2013

OTHER PUBLICATIONS

Communication dated Jan. 8, 2016 issued by the European Patent Office in counterpart European Patent Application No. 15186000.4.

*Primary Examiner* — Gregory M Desire
(74) *Attorney, Agent, or Firm* — Sughrue Mion, PLLC

(57) ABSTRACT

An apparatus and method for supporting computer aided diagnosis (CAD). The apparatus includes: a control processor configured to determine a duration during which a remaining image of a first region of interest (ROI) detected from a first image frame is displayed, based on a characteristic of measuring the first ROI; and a display configured to mark a remaining image of a second ROI of a second image frame in the first image frame and display the marked image on a screen, in response to the first image frame being acquired during a duration set to display the remaining image of the second ROI. the first image frame is obtained subsequent to the second image frame.

20 Claims, 13 Drawing Sheets

(56) References Cited

U.S. PATENT DOCUMENTS

| | | | | |
|---|---|---|---|---|
| 7,949,167 B2* | 5/2011 | Krishnan | ............ | G06F 19/3443 |
| | | | | 378/4 |
| 8,051,386 B2 | 11/2011 | Rosander et al. | | |
| 8,364,698 B2* | 1/2013 | Delgo | ................. | G06F 17/3079 |
| | | | | 707/769 |
| 8,460,192 B2* | 6/2013 | Yoshiara | ................. | A61B 8/08 |
| | | | | 600/407 |
| 8,718,340 B2* | 5/2014 | Madabhushi | ........ | G06K 9/3233 |
| | | | | 382/128 |
| 8,885,898 B2* | 11/2014 | Liu | ...................... | G06K 9/6215 |
| | | | | 382/128 |
| 2009/0041322 A1* | 2/2009 | Wolf | ........................ | G06K 9/44 |
| | | | | 382/131 |
| 2009/0148010 A1* | 6/2009 | Boroczky | ............ | G06K 9/3233 |
| | | | | 382/128 |
| 2016/0093046 A1* | 3/2016 | Jeon | ...................... | G06T 7/0012 |
| | | | | 382/128 |

* cited by examiner

410

420

APPARATUS AND METHOD FOR SUPPORTING COMPUTER AIDED DIAGNOSIS

CROSS-REFERENCE TO RELATED APPLICATION

This application claims priority from Korean Patent Application No. 10-2014-0129559, filed on Sep. 26, 2014, in the Korean Intellectual Property Office, the entire disclosure of which is incorporated herein by reference for all purposes.

BACKGROUND

1. Field

Apparatuses and methods consistent with exemplary embodiments relate to a Computer Aided Diagnosis (CAD) technique, and more particularly to technically supporting computer aided diagnosis.

2. Description of the Related Art

The computer aided diagnosis (CAD) system analyzes various medical images, such as ultrasound images, and marks suspected regions based on the analysis to help doctors in diagnosis of diseases. Such CAD system may reduce uncertainty in diagnosis that is inevitably caused by humans' limited identification ability, and may relieve doctors of heavy tasks of reading each and every medical image.

In the case in which a user moves a probe to identify medical images using the CAD system in real time, if a region of interest detected by the CAD system is too small or if a probe moves too fast, a region of interest displayed on a screen will disappear before a user checks the detected region.

SUMMARY

According to an aspect of an exemplary embodiment, there is provided an apparatus for supporting computer aided diagnosis (CAD) including: a control processor configured to determine a duration during which a remaining image of a first region of interest (ROI) detected from a first image frame is displayed, based on a characteristic of measuring the first ROI; and a display configured to mark a remaining image of a second ROI of a second image frame in the first image frame and display the marked image on a screen, in response to the first image frame being acquired during a duration set to display the remaining image of the second ROI. The first image frame may be obtained subsequent to the second image frame.

The control processor may determine the duration of displaying the remaining image of the first ROI based on at least one of a predetermined duration of displaying the remaining image of the first ROI, reliability of a detection result of the first ROI; a size of the detected first ROI; and a movement speed of an image scanner used to acquire the first and second image frames.

The control processor may be further configured to determine the duration of displaying the remaining image of the first ROI in direct proportion to the reliability of the detection result of the first ROI.

The control processor may be further configured to determine the duration of displaying the remaining image of the first ROI in inverse proportion of the size of the detected first ROI.

The control processor may be further configured to determine the duration of displaying the remaining image of the first ROI to be a period that ends when the speed of the image scanner is below a predetermined threshold, or a moving direction of the image scanner is opposite to a previous moving direction.

The image scanner may be a probe, and the apparatus may further include a probe speed detector configured to detect the movement speed of the probe.

The display may be further configured to terminate, according to a user's instruction, the displaying the remaining image of the second image frame, which is displayed in the first image frame.

The display may be further configured to display, in the first image frame, the remaining image of the second ROI that is distinguished from the first ROI of the first image frame.

The display may be further configured to display, in the first image frame, the remaining image of the second ROI by using different colors, brightness, transparency, types of lines, or marking shapes, according to elapsed time.

The display may be further configured to display the remaining image of the second ROI at a position of the first image frame that is predicted based on a scanning path of an image scanner used to acquire the first and second image frames.

The display may be further configured to display on a screen at least one of results of ROIs detected up to a present time, diagnosis results of ROIs detected from the first image frame or detected up to the present time, locations of ROIs unrecognized by a user among regions of interest detected up to the present time, and guide information for redetecting an ROI unrecognized by the user.

The results of ROIs detected up to the present time may include at least one of a total number of ROIs detected up to the present time; a number of ROIs that have been checked by the user among the ROIs detected up to the present time; and a number of ROIs that have not been checked by the user among the ROIs detected up to the present time.

The control processor may be further configured to determine whether a user checks the second ROI based on whether a movement speed of an image scanner used to acquire the second image frame is reduced below a predetermined threshold when detecting the second ROI, or based on whether a moving direction of the image scanner used when detecting the second ROI is changed to a previous moving direction.

The guide information may include at least one of information about time elapsed since detection of an ROI unrecognized by the user, and information about moving directions of an image scanner for redetecting the ROI unrecognized by the user.

The control processor may include an ROI detector configured to detect the first ROI from the first image frame.

According to an aspect of another exemplary embodiment, there is provided a method of supporting computer aided diagnosis (CAD) including: determining a duration during which a remaining image of a first region of interest (ROI) detected from a first image frame is displayed, based on a characteristic of measuring the first ROI; and marking a remaining image of a second ROI of a second image frame in the first image frame and displaying the marked image on a screen, in response to the first image frame being acquired during a duration set to display the remaining image of the second ROI. The first image frame may be obtained subsequent to the second image frame.

The determining the duration may include determining the duration of displaying the remaining image of the first ROI based on at least one of a predetermined duration of displaying the remaining image of the first ROI; reliability of a detection result of the first ROI; a size of the detected first ROI; and a movement speed of an image scanner used to acquire the first and second image frames.

The determining the duration may include determining the duration in direct proportion to the reliability of the detection result of the first ROI.

The determining the duration may include determining the duration in inverse proportion of the size of the detected first ROI.

The determining the duration may include determining the duration to be a period that ends when the speed of the image scanner is below a predetermined threshold, or a moving direction of the image scanner is opposite to a previous moving direction.

The method may further include detecting the speed of the image scanner.

The method may further include terminating, according to a user's instruction, displaying the remaining image of the second image frame, which is displayed in the first image frame.

The displaying may include displaying, in the first image frame, the remaining image of the second ROI that is distinguished from the first ROI of the first image frame.

The displaying may include displaying, in the first image frame, the remaining image of the second ROI by using different colors, brightness, transparency, types of lines, and marking shapes, according to elapsed time.

The displaying may include displaying the remaining image of the second ROI at a position of the first ROI that is predicted based on a scanning path of an image scanner used to acquire the first and second image frames.

The displaying may include displaying on the screen at least one of results of ROIs detected up to a present time; diagnosis results of ROIs detected from the first image frame or detected up to the present time; locations of ROIs unrecognized by a user among ROIs detected up to the present time; and guide information for redetecting ROIs unrecognized by the user.

The results of ROIs detected up to the present time may include at least one of a total number of ROIs detected up to the present time; a number of ROIs that have been checked by the user among the ROIs detected up to the present time; and a number of ROIs that have not been checked by the user among the ROIs detected up to the present time.

The method may further include determining whether the user checks the second ROI based on whether a movement speed of an image scanner used to acquire the first and second image frames is reduced below a predetermined threshold when detecting the second ROI, or based on whether a moving direction of the image scanner used when detecting the second ROI is changed to a previous moving direction.

The guide information may include at least one of information about time elapsed since detection of an ROI unrecognized by the user, and information about moving directions of an image scanner for redetecting the ROI unrecognized by the user.

The method may further include detecting the first ROI from the first image frame.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
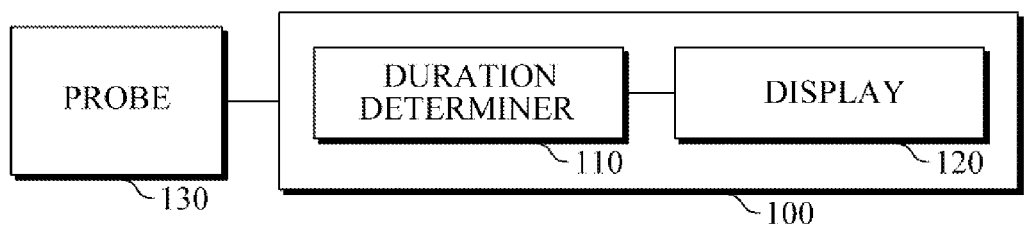
FIG. 1 is a block diagram illustrating an example of an apparatus for supporting computer aided diagnosis (CAD).

Exemplary embodiments are described in greater detail below with reference to the accompanying drawings.

In the following description, like drawing reference numerals are used for like elements, even in different drawings. The relative size and depiction of these elements may be exaggerated for clarity, illustration, and convenience. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Throughout the present description, a remaining image of a region of interest (ROI) refers to an image of an ROI detected in a previous image frame and remains in a subsequent image frame although the image is not detected in a subsequent frame image. Further, the duration of displaying a remaining image of an ROI refers to a duration during which the remaining image is displayed in an image frame, and the duration may be set in units of frames or time.

FIG. 1 is a block diagram illustrating an example of an apparatus for supporting computer aided diagnosis (CAD).

Referring to FIG. 1, an apparatus 100 for supporting CAD (hereinafter referred to as a "CAD supporting apparatus") includes a control processor (e.g., a duration determiner 110) and an display 120.

The duration determiner 110 may determine a duration during which a remaining image of a region of interest detected from a current image frame is displayed. The region of interest may include not only a malignant lesion, but also a lesion area that may be determined as malignant or benign, or a region with special features.

In one exemplary embodiment, in the case in which there is a predetermined duration of displaying a remaining image, such as a duration set by default or a duration set by a user, the duration determiner 110 may determine the predetermined displaying duration as a duration during which a region of interest is displayed in a current frame image.

In another exemplary embodiment, the duration determiner 110 may determine a duration of displaying a region of interest in a current frame image based on reliability or accuracy of a detection result of a region of interest. For example, in the case of a high reliability or accuracy of a detection result of a region of interest, the duration determiner 110 may determine a relatively longer duration of displaying a remaining image, and in the case of a low reliability or accuracy of a detection result of a region of interest, the duration determiner 110 may determine a relatively shorter duration of displaying a remaining image. That is, the duration determiner 110 may determine a duration of displaying a remaining image in direct proportion to the reliability or accuracy of a detection result of a region of interest.

In yet another exemplary embodiment, the duration determiner 110 may determine a duration of displaying a region of interest in a current frame image based on the size of a detected region of interest. For example, in the case in which a detected region of interest is large, the duration determiner 110 may determine a relatively shorter duration of displaying a region of interest, and in the case in which a detected region of interest is small, the duration determiner 110 may determine a relatively longer duration of displaying a region of interest. That is, the duration determiner 110 may determine a duration of displaying a retained image in direct proportion to the size of a region of interest. For example, the duration determiner 110 may determine a duration by using the following Equation 1.

$$T = \text{Max}\{\text{the size of a region of interest}, C - \text{the size of a region of interest}\}, \quad \text{[Equation 1]}$$

in which T represents a duration of displaying a remaining image, and C represents a constant value. The constant value C may be set based on system performance or usage purposes.

The size of a region of interest may be determined based only on a region of interest in a current frame image, or may be determined based on regions of interest successively detected in multiple image frames.

In still another exemplary embodiment, the duration determiner 110 may determine a duration of displaying a remaining image in a current frame image based on the speed of an image scanner (e.g., a probe 130) used to acquire an image frame. The probe 130 may be an ultrasonic transducer or a fiber optic probe which is used in generating cross-sectional images of various parts of a body.

For example, the duration determiner 110 may determine a duration during which a remaining image of a current image frame is displayed until the speed of the probe 130 is reduced below a predetermined threshold, or until the probe 130 is moved in an opposite direction of a previous moving direction.

That is, the CAD supporting apparatus 100 determines an endpoint of a time period during which a remaining image of a region of interest is displayed in a current frame image. The remaining image of the region of interest in the current image frame may be displayed in a subsequent image frame until a user recognizes the remaining image of the region of interest in the current frame image. In this case, by checking whether the speed of the probe 130 is reduced below a predetermined threshold, or by checking whether the probe 130 moves in an opposite direction of a previous moving direction, it may be determined whether the user checks the remaining image of the region of interest.

In another example, the duration determiner 110 may determine a relatively longer duration of displaying a remaining image in the case in which the speed of the probe 130 is fast, or may determine a relatively shorter duration of displaying a remaining image in the case in which the speed of the probe 130 is slow. That is, the duration determiner 110 may determine a duration of displaying a remaining image in direct proportion to the speed of the probe 130.

The display 120 may mark a detected region of interest in a current frame image, and may output the marked region on a screen. For example, the display 120 may display a location of the detected region of interest in a current image by using a bounding box, or by marking the center of the region with a dot or a cross. However, a method of displaying a region of interest is not limited thereto, and a region of interest may be displayed by many methods, including a method of displaying by using various shapes of distinguished marks, such as round, triangle, or the like, or displaying by color coding with various colors.

If a current frame image is acquired within a duration predetermined for displaying a remaining image of a previous frame, the display 120 may display in the current image frame the remaining image of a region of interest of the previous image frame. The CAD supporting apparatus 100 may display a remaining image of a region of interest of the current image frame in a subsequent image frame for the duration predetermined for displaying the remaining image of the current image frame.

In one exemplary embodiment, the display 120 may display a remaining image of a region of interest of a previous image frame that is distinguished from a region of interest of a current image frame. For example, the display 120 may display a remaining image of a region of interest of a previous image frame by using different colors, transparency, types of lines (e.g., dotted line, solid line, etc.), and marking shapes (e.g., dot, cross, circle, square, etc.) so that a distinguished mark of a region of interest in a current image frame may be different from the region of interest in the previous image frame.

In another exemplary embodiment, when displaying a remaining region-of-interest image of a previous image frame in a current image frame, the display 120 may use different colors, brightness, transparency, types of lines, marking shapes, and the like according to elapsed time. In this manner, a user may predict elapsed time even without checking the region of interest of the previous image frame.

In yet another exemplary embodiment, the display 120 may display a remaining region-of-interest image of a previous image frame in a current image frame at a position that is predicted based on a location change of a region of interest in a previous image frame. The location change of the region of interest in the previous image frame may be predicted based on a scanning path of the probe 130 used to acquire image frames.

In response to a user's instruction, the display 120 may terminate displaying the remaining region of the previous frame image which is displayed in the current image frame.

The display 120 may output on a screen: information on results of regions of interest detected up to the present time; regions of interest detected from a current image frame; diagnosis results of regions of interest detected up to the present time; information on locations of regions of interest unrecognized by the user among regions of interest detected up to the present time; guide information for redetecting regions of interest unrecognized by the user; and the like.

The results of regions of interest detected up to the present time may include: a total number of regions of interest detected up to the present time; a number of regions of interest that have been checked by the user among the regions of interest detected up to the present time; a number of regions of interest that have not been checked by the user among the regions of interest detected up to the present time; and the like. Further, the guide information may include information about the time elapsed since detection of a region of interest unrecognized by the user, information about moving directions of the probe 130 for redetecting regions of interest unrecognized by the user, and the like.

The CAD supporting apparatus 100 may determine whether a user checks a region of interest based on a speed and a moving direction of the probe 130 used when detecting a region of interest. Specifically, if the probe speed is reduced below a predetermined threshold, or the moving direction of the probe is changed to a previous moving direction, the CAD supporting apparatus 100 may determine that the user has checked the region of interest.

Further, the guide information may be generated based on locations of regions of interest input by the user, based on locations of regions of interest determined by an external sensor or a camera, based on the speed of the probe 130, or the like.

The display 120 may output, in a screen area other than an area where a current image frame is displayed, or on a separate screen from a screen where a current image frame is output, information on results of regions of interest detected up to the present time, a diagnosis result of a region of interest detected in a current image frame or regions of interest detected up to the present time, information on locations of regions of interest unrecognized by the user among regions of interest detected up to the present time, guide information for redetecting regions of interest unrecognized by the user, and the like, so that the display of information does not disturb diagnosis of the user. Further, the display 120 may emphasize information that is determined to be significant information (e.g., a number of regions of interest unrecognized by the user, etc.) by using colors, blinking, and the like.

Figure 2:
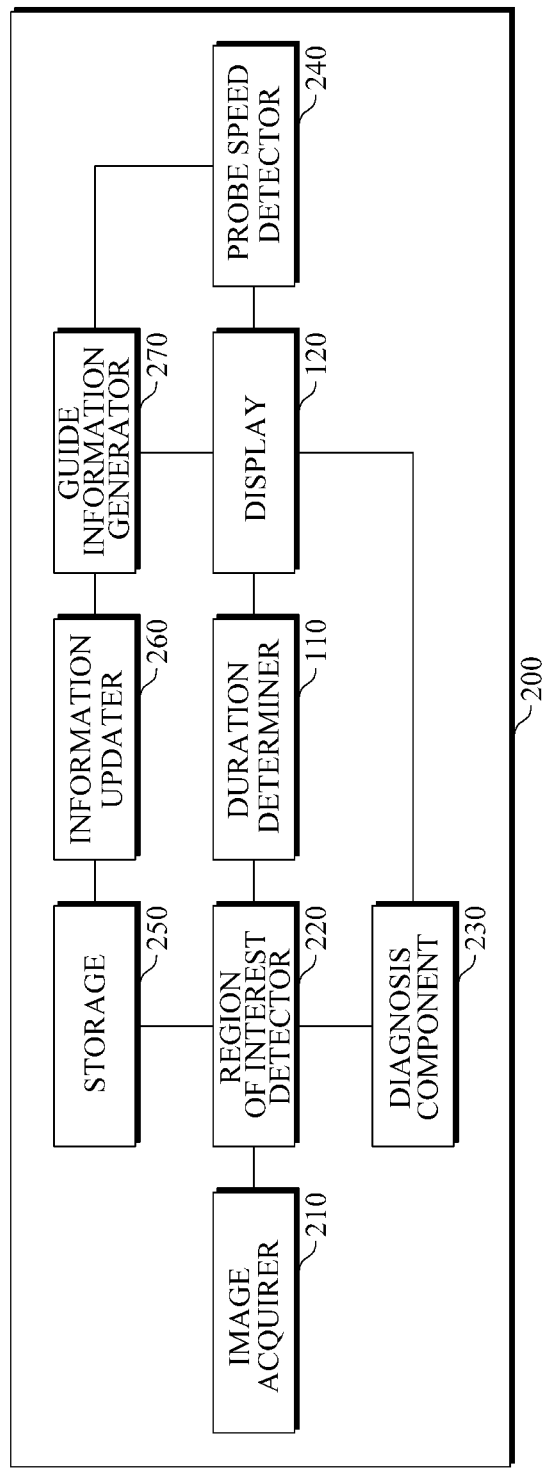
FIG. 2 is a block diagram illustrating another example of an apparatus for supporting CAD.

FIG. 2 is a block diagram illustrating another example of an apparatus for supporting CAD.

Referring to FIG. 2, a CAD supporting apparatus 200 may further include an image acquirer 210, a region of interest detector 220, a diagnosis component 230, a probe speed detector 240, a storage 250, an information updater 260, and a guide information generator 270, in addition to the duration determiner 110 and the display 120 illustrated in FIG. 1. At least one of the region of interest detector 220, the diagnosis component 230, the information updater 260, and the duration determiner 110 may be implemented by a control processor.

The image acquirer 210 may acquire a patient's medical images. The medical images may be ultrasound images acquired in units of frames by using a probe 130 in real time.

The region of interest detector 220 may detect a region of interest by analyzing a current image frame acquired in real time by the image acquirer 210. For example, the region of interest detector 220 may detect a region of interest from a current image frame by using an automatic lesion detection algorithm. The automatic lesion detection algorithm may include AdaBoost, Deformable Part Models (DPM), Deep Neural Network (DNN), Convolutional Neural Network (CNN), Sparse Coding, and the like, but is not limited thereto.

The diagnosis component 230 may diagnose a region of interest detected by the region of interest detector 220. For example, the diagnosis component 230 may diagnose a region of interest detected by using a lesion detection algorithm. The lesion classification algorithm may include Support Vector Machine (SVM), Decision Tree, Deep Belief Network (DBN), Convolutional Neural Network (CNN), and the like, but is not limited thereto.

The probe speed detector 240 may detect the speed of the probe 130.

In one exemplary embodiment, the probe speed detector 240 may detect the probe speed based on a difference between a sum of image intensities of pixels of a previous image frame and a sum of image intensities of pixels of a current image frame acquired through the probe 130. That is, the probe speed detector 240 may preprocess images to calculate the image intensities of the pixels of the previous image frame and the image intensities of the pixels of the current image frame, and may add up the calculated image intensities of the pixels of the previous image frame and the calculated image intensities of the pixels of the current image frame, so that the probe speed may be detected based on the difference between the sum of image intensities for the pixels of the previous image frame and the sum of image intensities for the pixels of the current image frame.

In another exemplary embodiment, the probe speed detector 240 may detect the probe speed based on a difference between histograms of the previous image frame and the current image frame. When the difference between the histogram of the previous frame image and the histogram of the current frame image is greater a value set by using a spectral analysis method, the probe speed detector 240 may determine the probe speed based on the difference.

In yet another exemplary embodiment, the probe speed detector 240 may detect the probe speed based on a change in information, such as salient regions of the previous image frame and the current image frame, and the like.

In still another exemplary embodiment, the probe speed detector 240 may detect the probe speed based on values of sensors, such as a three axis accelerometer sensor mounted on the probe 130, and the like.

The storage 250 may store results of regions of interest detected up to the present time, diagnosis results of regions of interest detected up to the present time, location information of regions of interest detected up to the present time, and the like.

The storage 250 may include flash memory type, hard disk type, multi-media card micro type, card type memory (e.g., SD or XD memory, etc.), random access memory (RAM), static random access memory (SRAM), read-only memory (ROM), electrically erasable programmable read only memory (EEPROM), programmable read only memory (PROM), magnetic memory, magnetic disks, optical discs, or the like.

The information updater 260 may update information stored in the storage 250 based on detection results of the region of interest detector 220, diagnosis results of the diagnosis component 230, a probe speed detected by the probe speed detector 240, information on probe locations determined using a sensor or a camera mounted inside or outside of the probe 130, and the like.

The information updater 260 may update information stored in the storage 250 based on information manually input by a user.

The guide information generator 270 may generate guide information for redetecting a region of interest based on a location of a region of interest input by a user, or based on a location of a region of interest determined by a sensor or a camera mounted inside or outside of the probe 130, a probe speed, or the like. The guide information may include information on the time elapsed since detection of a region of interest unrecognized by the user, information on moving directions of the probe 130 for redetecting a region of interest unrecognized by the user, and the like.

Figure 3:
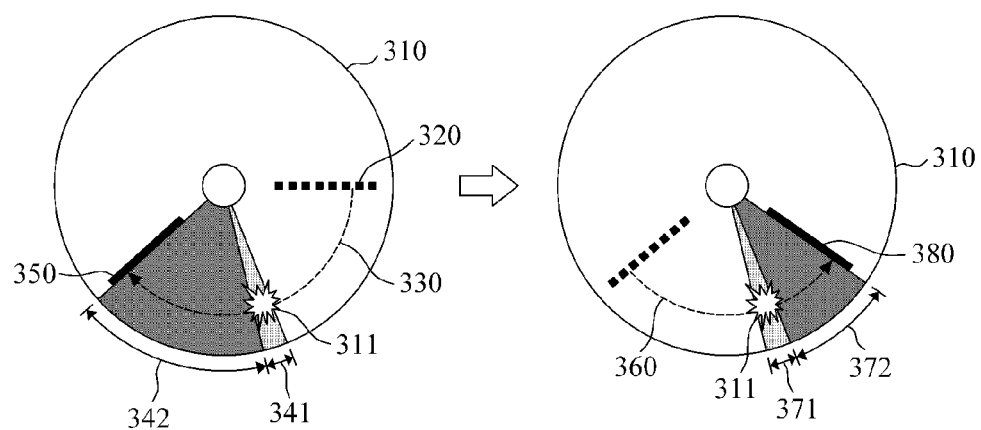
FIG. 3 is a diagram illustrating an example of determining a duration during which a remaining image of a region of interest (ROI) is displayed on the screen by apparatuses 100 and 200 for supporting CAD.

FIG. 3 is a diagram illustrating an example of determining a duration during which a remaining image of a region of interest (ROI) is displayed on the screen by apparatuses 100 and 200 for supporting CAD.

Once a user scans a lesion 310 by moving the probe 130 in a specific direction 330 from a scan starting point 320, the region of interest detector 220 detects a region of interest 311 from an image frame at a specific location. In this case, the region of interest detector 220 may detect the region of interest 311 from image frames acquired for a specific period of time 341.

The duration determiner 110 determines a duration 342 of displaying a remaining image of the region of interest 311 to be a period until a point in time 350 at which the probe speed becomes below a predetermined threshold, or a moving direction of the probe 130 becomes opposite to the previous moving direction 330. The display 120 displays the remaining image of the region of interest 311 in a current image frame until the point in time 350 at which the probe speed becomes below the predetermined threshold, or the moving direction of the probe 130 is opposite to the previous moving direction 330. In this case, the CAD supporting apparatus 100 and 200 may determine that the point in time 350 at which the probe speed becomes below the predetermined threshold, or the moving direction of the probe 130 becomes opposite to the previous moving direction 330 is a point in time at which the user of the probe 130 recognizes the region of interest 311.

Once the user redetects the lesion 310 of a patient while moving the probe 130 in the direction 360 opposite to the previous moving direction 330, the region of interest detector 220 detects the region of interest 311 from the image frame at the specific location.

The duration determiner 110 may determine a duration 372 of displaying a remaining image of a detected region of interest to be a period until the point in time 380 at which the probe speed becomes below the predetermined threshold, or the moving direction of the probe 130 becomes opposite to the previous moving direction 360. The display 120 displays the remaining image of the region of interest 311 during the determined duration 372, i.e., until the point in time 380 at which the probe speed becomes below the predetermined threshold, or the moving direction of the probe 130 becomes opposite to the previous moving direction 360.

Figure 4A:
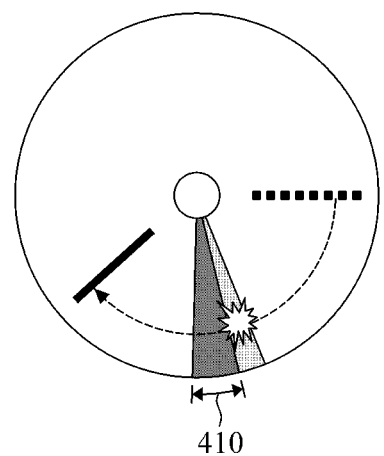
FIGS. 4A and 4B are diagrams illustrating another example of determining a duration during which a remaining image of an ROI is displayed on the screen by apparatuses 100 and 200 for supporting CAD.
Figure 4B:
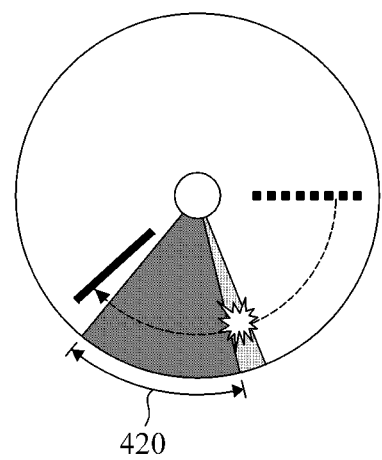

FIGS. 4A and 4B are diagrams illustrating another example of determining duration of displaying a remaining image of an ROI on the screen by apparatuses 100 and 200 for supporting CAD. More specifically, FIG. 4A illustrates an example of determining a duration of displaying a remaining image of a region of interest in the case of a low reliability of detection results of a region of interest, and FIG. 4B illustrates an example of determining a duration of displaying a remaining image of a region of interest in the case of a high reliability of detection results of a region of interest.

Referring to FIGS. 4A and 4B, the duration determiner 110 may determine a duration of displaying a region of interest in direct proportion to a reliability of detection results of a region of interest. That is, in the case of a low reliability of detection results of a region of interest, the duration determiner 110 may determine a relatively shorter duration 410 of displaying a remaining image of a region of interest, and in the case of a high reliability of detection results of a region of interest, the duration determiner 110 may determine a relatively longer duration 420 of displaying a remaining image of a region of interest.

Figure 5A:
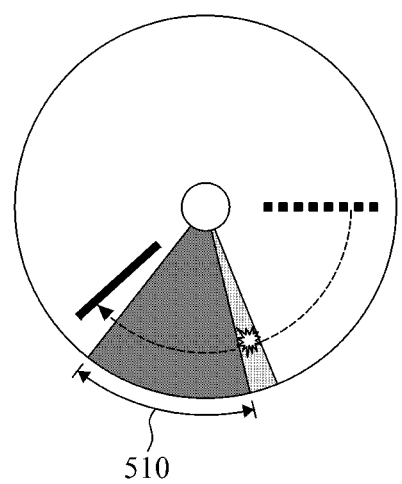
FIGS. 5A and 5B are diagrams illustrating yet another example of determining a duration during which a remaining image of an ROI is displayed on the screen by apparatuses 100 and 200 for supporting CAD.
Figure 5B:
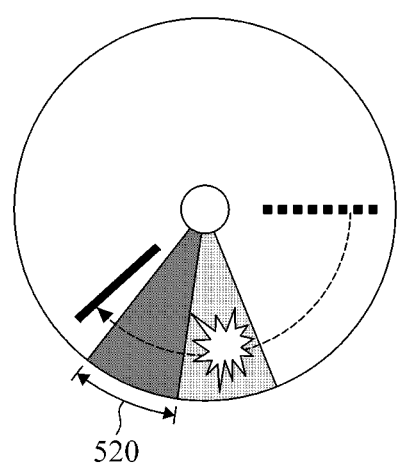

FIGS. 5A and 5B are diagrams illustrating yet another example of determining duration of displaying a remaining image of an ROI on the screen by apparatuses 100 and 200 for supporting CAD. More specifically, FIG. 5A illustrates an example of determining a duration of displaying a remaining image in the case in which a detected region of interest is small, and FIG. 5B illustrates an example of determining a duration of displaying a remaining image in the case in which a detected region of interest is large.

Referring to FIGS. 5A and 5B, the duration determiner 110 may determine a duration of displaying a remaining image of a region of interest in inverse proportion to the size of a detected region of interest. That is, the duration determiner 110 may determine a relatively shorter duration 510 of displaying the remaining image of the region of interest in the case in which the detected region of interest is small, and may determine a relatively longer duration 520 of displaying the remaining image of the region of interest in the case in which the detected region of interest is large.

Figure 6:
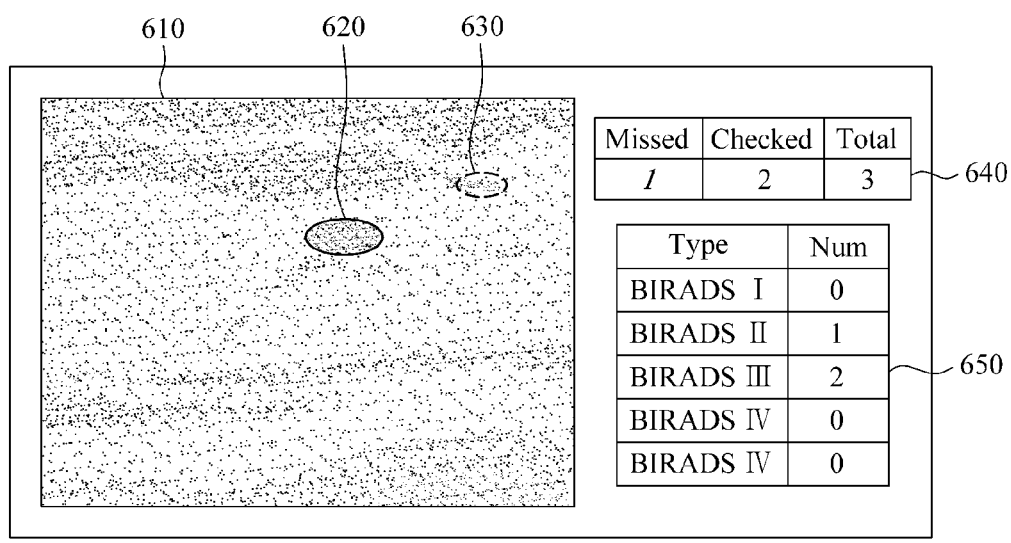
FIG. 6 is a diagram illustrating an example of an image displayed on a screen output by an display 120.

FIG. 6 is a diagram illustrating an example of an image displayed on a screen output by an display 120, in which it is assumed that an input image is an ultrasound breast image, and a current image frame is acquired during a duration of displaying a remaining image of a previous image frame. Such assumption is also applied to FIGS. 7A, 7B, and 8.

Referring to FIG. 6, the display 120 may display in a current image frame 610 a region of interest 620 detected from the current image frame 610, and a remaining image 630 of a region of interest of a previous image frame. The region of interest 620 of the current image frame 610 is shown in a circle with a solid line, and the remaining image 630 of the region of interest of a previous image frame is shown in a circle with a dotted line.

Further, the display 120 may output, in a specific screen area that does not disturb the observation of the current frame image 610, a result 640 of regions of interest detected up to the present time and a diagnosis result 650 of regions of interest detected up to the present time.

In the exemplary embodiment, based on the result 640 of regions of interest detected up to the present time, it can be understood that the total number of regions of interest detected up to the present time is three, among which one region of interest was unrecognized by a user, while the other two were checked by the user. Further, based on the diagnosis result 650 of regions of interest detected up to the present time, it can be understood that among three regions of interest in total, one shows benign findings of BI-RADS category 2, while the other two show probably benign findings of BI-RADS category 3.

The display 120 may also emphasize information determined to be significant information (e.g., a number of regions of interest unrecognized by the user, etc.) by using colors, blinking, or the like.

Figure 7A:
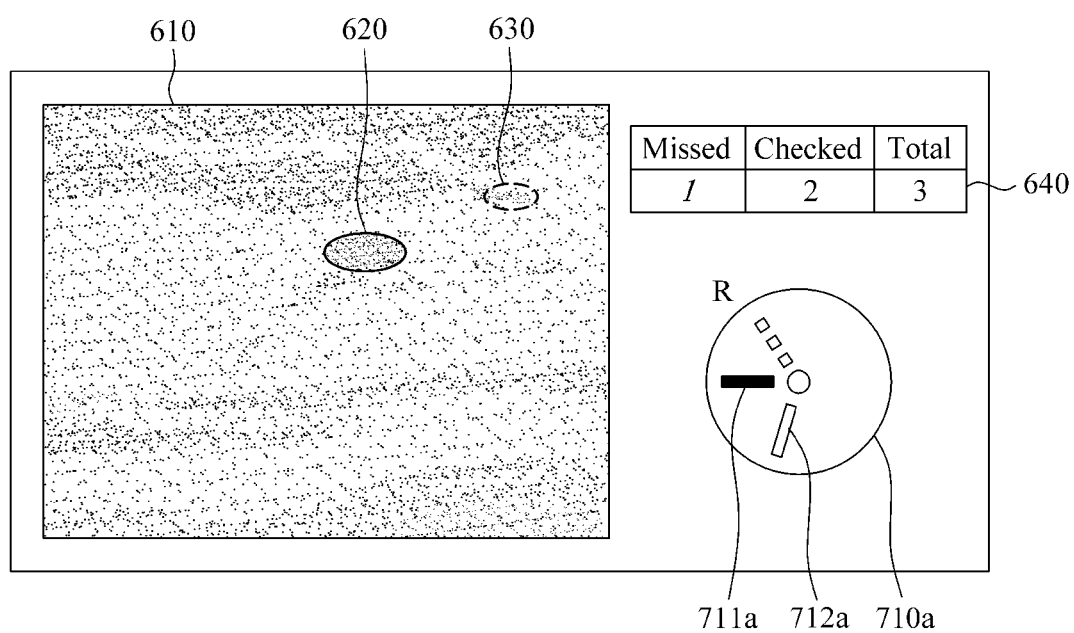
FIGS. 7A and 7B are diagrams illustrating another example of an image displayed on a screen output by an display 120.
Figure 7B:
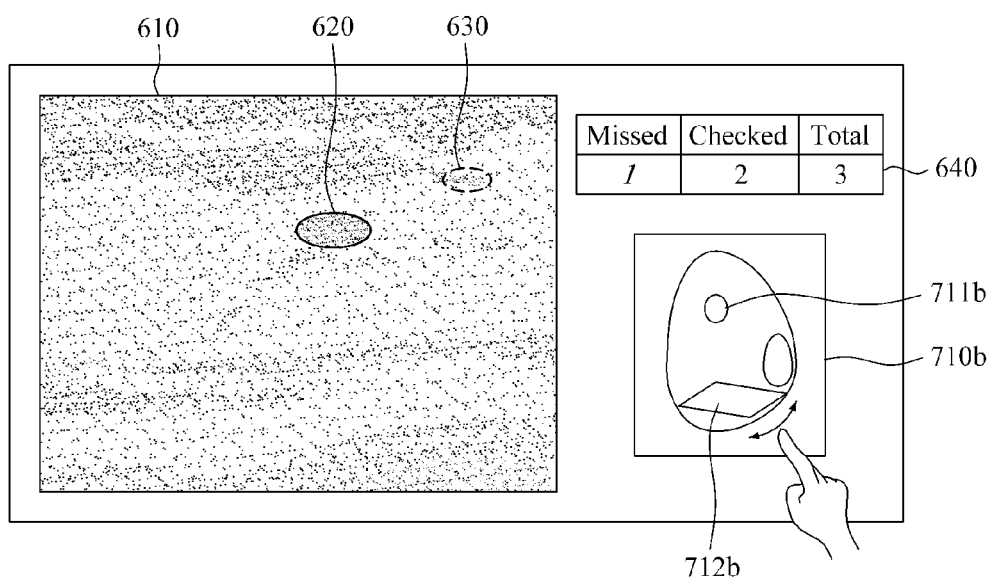

FIGS. 7A and 7B are diagrams illustrating another example of an image displayed on a screen output by an display 120. More specifically, FIG. 7A illustrates an example of displaying a two-dimensional image of a location of a region of interest unrecognized by a user, and FIG. 7B illustrates an example of displaying a three-dimensional image of a location of a region of interest unrecognized by the user.

Referring to FIGS. 7A and 7B, the display 120 may display, in a current image frame 610, a region of interest 620 detected from the current image frame 610 and a remaining image 630 of a region of interest of a previous image frame. The region of interest 620 of the current image frame 610 is shown in a circle with a solid line, and the region of interest 630 of a previous image frame is shown in a circle with a dotted line.

The display 120 may output, in a specific screen area that does not disturb the observation of the current frame image 610, a result 640 of regions of interest detected up to the present time and locations 710a and 710b of regions of interest unrecognized by the user.

In this case, reference numerals 711a and 711b denote locations of regions of interest unrecognized by the user, and reference numerals 712a and 712b denote a current location of the probe 130.

The locations 710a and 710b of regions of interest unrecognized by the user may be predicted based on the location of the probe 130 intermittently input by the user, and may be predicted based on sensor values of various sensors mounted on the probe.

Figure 8:
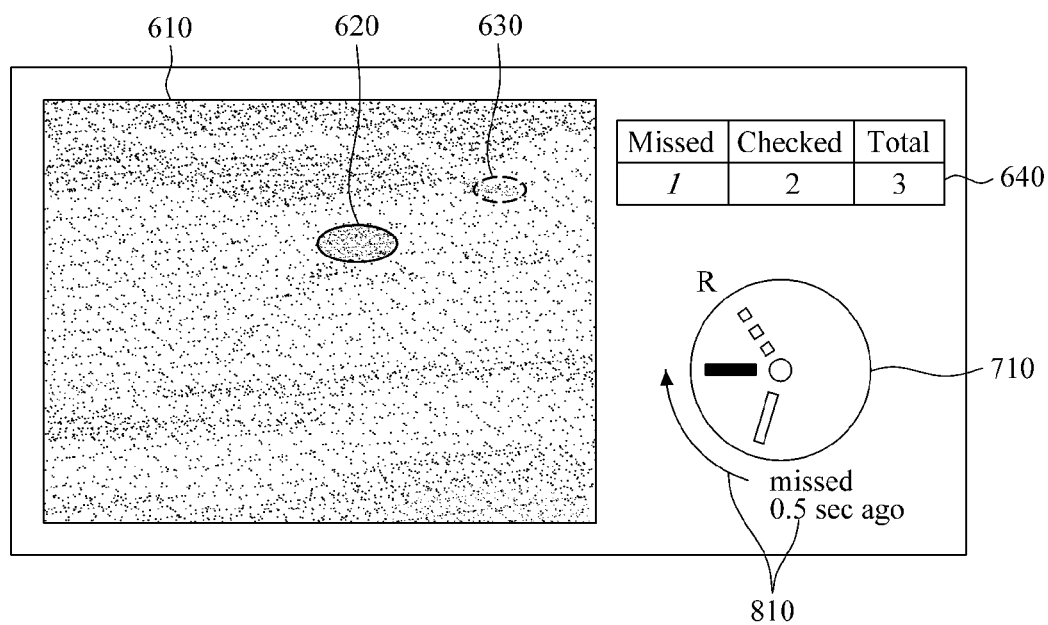
FIG. 8 is a diagram illustrating yet another example of an image displayed on a screen output by an display 120.

FIG. 8 is a diagram illustrating yet another example of an image displayed on a screen output by an display 120.

Referring to FIG. 8, the display 120 may display, in a current image frame 610, a region of interest 620 detected from the current image frame 610 and a remaining image 630 of a region of interest of a previous image frame. The region of interest 620 of the current image frame 610 is shown in a circle with a solid line, and the remaining image 630 of the previous image frame is shown in a circle with a dotted line.

The display 120 may output, in a specific screen area that does not disturb the observation of the current frame image 610, a result 640 of regions of interest detected up to the present time, a location 710 of a region of interest unrecognized by the user, and guide information 810 for redetecting the unrecognized region of interest. The guide information 810 may include information on the time elapsed since detection of the region of interest unrecognized by the user, and information on moving directions of the probe 130 for redetecting the region of interest unrecognized by the user.

The guide information may be generated based on locations of regions of interest input by the user, locations of regions of interest determined by a sensor or a camera inside or outside of the probe 130, the speed of the probe 130, and the like.

Figure 9:
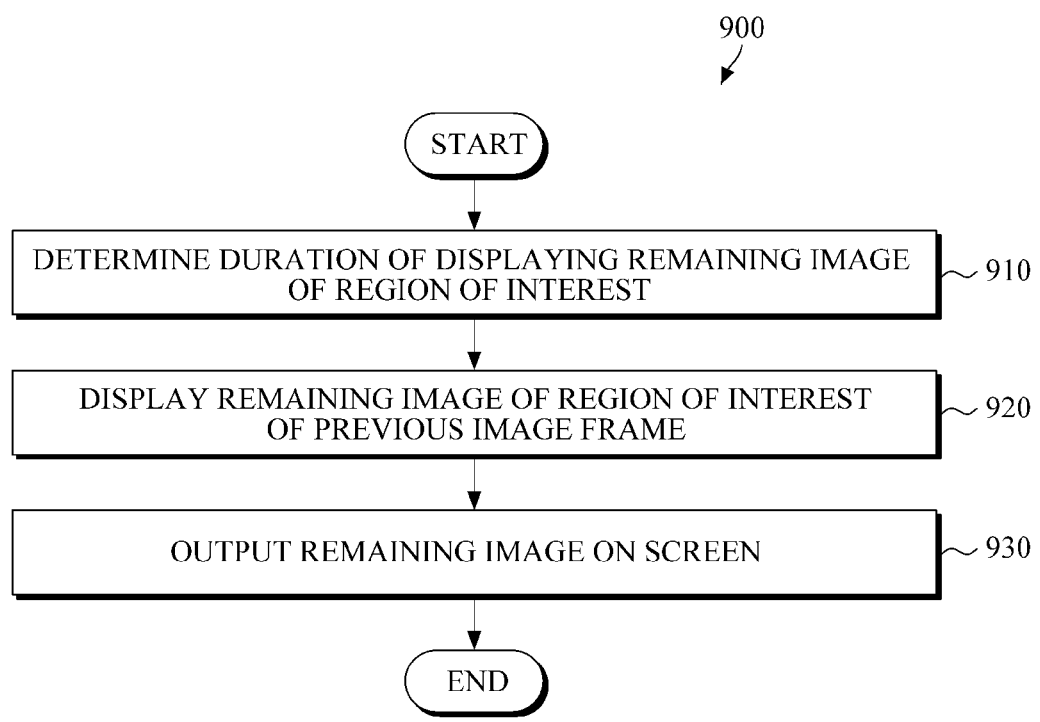
FIG. 9 is a flowchart illustrating a method of supporting CAD.

FIG. 9 is a flowchart illustrating a method of supporting CAD.

Referring to FIG. 9, the method 900 of supporting CAD (hereinafter referred to as a "CAD supporting method") includes determining a duration for displaying a remaining image of a region of interest detected from a current image frame (operation 910).

In one exemplary embodiment, in the case in which there is a predetermined duration of displaying a remaining image of a region of interest, such as a duration set by default, or a duration set by the user, the CAD supporting apparatuses 100 and 200 may determine the predetermined duration to be a duration of displaying a remaining image of a region of interest of a current image frame.

In another exemplary embodiment, the CAD supporting apparatuses 100 and 200 may determine a duration of displaying a remaining image of a region of interest based on the reliability or accuracy of detection results of regions of interest. For example, the CAD supporting apparatuses 100 and 200 may determine a duration of displaying a remaining image of a region of interest in direct proportion to the reliability or accuracy of detection results of a region of interest.

In yet another exemplary embodiment, the CAD supporting apparatuses 100 and 200 may determine a duration of displaying a remaining image of a region of interest of a current image frame based on the size of a detected region of interest. For example, the CAD supporting apparatuses 100 and 200 may determine a duration of displaying a remaining image of a region of interest in inverse proportion to the size of a detected region of interest. For example, the CAD supporting apparatuses 100 and 200 may determine a duration of displaying a region of interest by using Equation 1.

In still another exemplary embodiment, the CAD supporting apparatuses 100 and 200 may determine a duration of displaying a remaining image of a region of interest of a current image frame based on the speed of the probe 130 used to acquire frame images. For example, the CAD supporting apparatuses 100 and 200 may determine a duration of displaying a remaining image of a region of interest of a current image frame to be a period until the probe speed is reduced below a predetermined threshold, or until the probe 130 moves in an opposite direction of a previous moving direction. In another example, the CAD supporting apparatuses 100 and 200 may determine a duration of displaying a remaining image in direct proportion to a probe speed.

Subsequently, in the case in which a current image frame is acquired during the predetermined duration of displaying a remaining image of a region of interest of a previous image frame, a remaining image of a region of interest of the previous image frame is displayed in a current image frame (operation 920).

In one exemplary embodiment, the CAD supporting apparatuses 100 and 200 may display a remaining image of a region of interest of a previous image frame that is distinguished from a region of interest of a current image frame. For example, the CAD supporting apparatuses 100 and 200 may display a remaining image of a region of interest of a previous image frame by using different colors, transparency, types of lines (e.g., dotted line, solid line, etc.), marking shapes (e.g., dot, cross, circle, square, etc.) so that a distinguished mark of a region of interest in a current image frame may be different from the region of interest in the previous image frame.

In another exemplary embodiment, when displaying a remaining region-of-interest image of a previous image frame in a current image frame, the CAD supporting apparatuses 100 and 200 may use different colors, brightness, transparency, types of lines, marking shapes, and the like according to elapsed time.

In yet another exemplary embodiment, the CAD supporting apparatuses 100 and 200 may display a remaining region-of-interest image of a previous image frame in a current image frame at a position that is predicted in consideration of a location change of a region of interest in a previous image frame.

Then, a current image frame, in which a remaining image of a region of interest of a previous image frame is displayed, is output on a screen (operation 930). A current image frame may be displayed on a screen with results of regions of interest detected up to the present time, diagnosis results of regions of interest detected from the current image frame or detected up to the present time, locations of regions of interest unrecognized by the user among regions of interest detected up to the present time, and guide information for redetecting regions of interest unrecognized by the user.

For example, the CAD supporting apparatuses 100 and 200 may display a current image frame, in which a remaining image of a region of interest of a previous image frame is displayed, with results of regions of interest detected up to the present time, diagnosis results of regions of interest detected from the current image frame or detected up to the present time, locations of regions of interest unrecognized by the user among regions of interest detected up to the present time, and guide information for redetecting regions of interest unrecognized by the user.

The results of regions of interest detected up to the present time may include a total number of regions of interest detected up to the present time, a number of regions of interest checked by the user among the regions of interest detected up to the present time, a number of regions of interest unrecognized by the user among the regions of interest detected up to the present time, and the like. Further, the guide information may include information on the time elapsed since detection of a region of interest unrecognized by the user, information on moving directions of the probe 130 for redetecting regions of interest unrecognized by the user, and the like.

Based on whether the speed of the probe 130 used when detecting a region of interest is reduced below a predetermined threshold, or based on whether a moving direction of the probe 130 used when detecting a region of interest is changed to a previous moving direction, it may be determined whether the user checks a region of interest or not.

Further, the guide information may be generated based on locations of regions of interest input by the user, based on locations of regions of interest determined by an external sensor or a camera mounted inside or outside of the probe 130, based on the speed of the probe 130, or the like.

Figure 10:
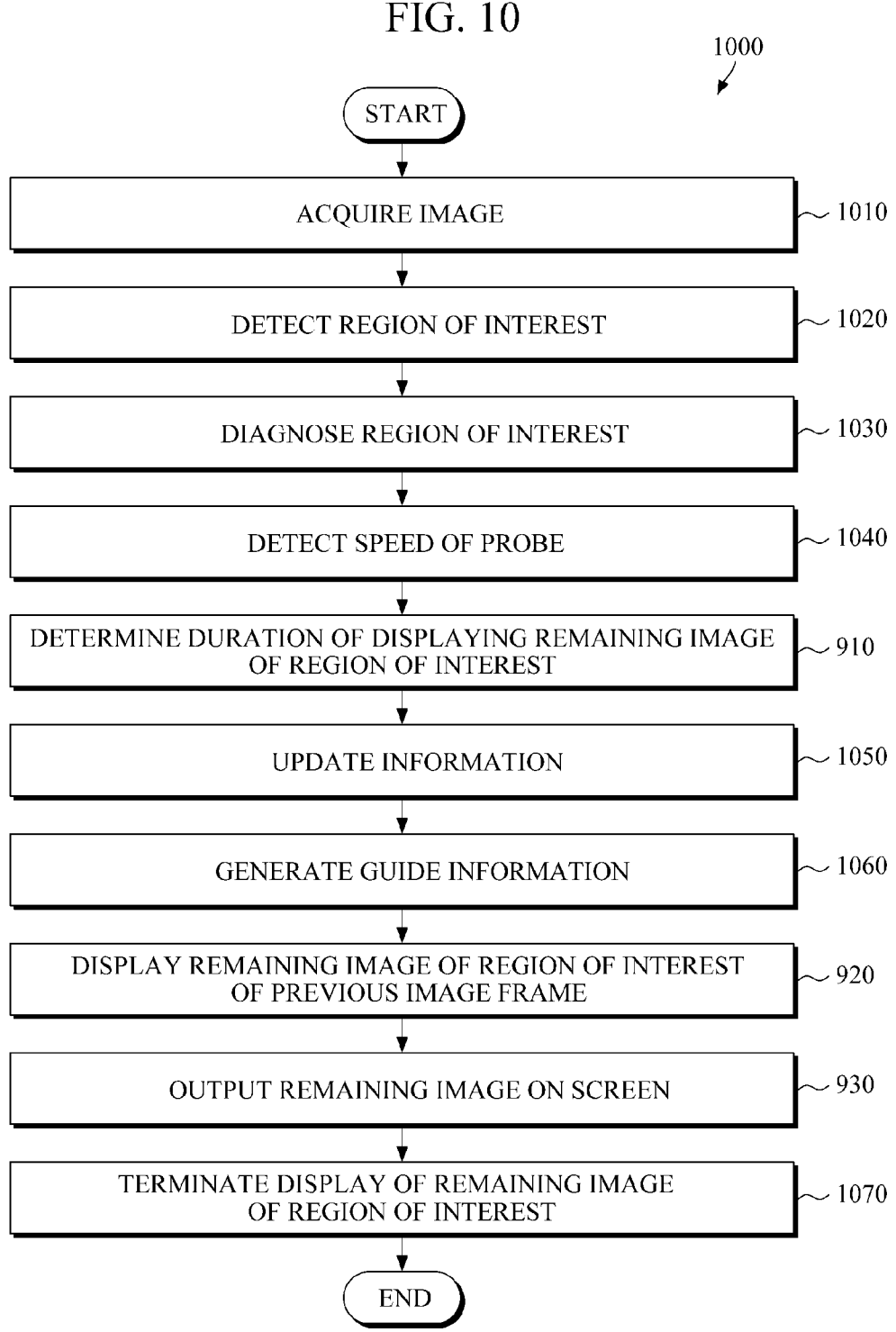
FIG. 10 is a flowchart illustrating another example of a method of supporting CAD.

FIG. 10 is a flowchart illustrating another example of a CAD supporting method.

Referring to FIG. 10, the CAD supporting method 1000 may further include selectively acquiring an image frame by using a probe 130 (operation 1010), detecting a region of interest from the current image frame (operation 1020), diagnosing the detected region of interest (operation 1030), detecting a speed of the probe 130 (operation 1040), updating information (operation 1050), generating guide information (operation 1060), and terminating displaying a remaining image of a region of interest (operation 1070) in addition to the CAD supporting method 900 in FIG. 9.

In operation 1010, a patient's medical image is acquired. The medical image may be an ultrasound image acquired in units of frames by using the probe 130 in real time.

In operation 1020, a region of interest is detected by analyzing a current image frame. For example, the CAD supporting apparatus 200 may detect a region of interest from a current image frame by using an automatic lesion detection algorithm, such as AdaBoost, Deformable Part Models (DPM), Deep Neural Network (DNN), Convolutional Neural Network (CNN), Sparse Coding, and the like.

In operation 1030, the detected region of interest is diagnosed. For example, the CAD supporting apparatus 200 may diagnose the detected region of interest by using Support Vector Machine (SVM), Decision Tree, Deep Belief Network (DBN), Convolutional Neural Network (CNN), and the like.

In operation 1040, a probe speed is detected. For example, the CAD supporting apparatus 200 may detect a probe speed based on a difference between the sum of image intensities for pixels of a previous image frame and the sum of image intensities for pixels of the current image frame acquired through the probe 130, based on a difference between histograms of the previous frame image and the current frame image, a change in information such as salient regions of the previous frame image and the current frame image, and the like, and based on values of sensors, such as a three axis accelerometer sensor mounted on the probe 130, and the like.

Upon detecting the region of interest, pre-stored information may be updated in operation 1050 based on diagnosis results of the detected region of interest, the detected speed of the probe 130, the location of the probe 130 determined by a sensor or a camera mounted inside or outside of the probe 130, information manually input by a user, and the like.

In operation 1060, guide information for redetecting the region of interest may be generated based on locations of regions of interest input by the user, locations of regions of interest determined by a sensor or a camera mounted inside or outside of the probe 130, the speed of the probe 130, and the like.

In operation 1070, displaying the remaining image of the region of interest of the previous image frame, which is displayed in the current image frame, is terminated according to the user's instruction.

While not restricted thereto, an exemplary embodiment can be embodied as computer-readable code on a computer-readable storage medium that includes program instructions to be implemented by a computer to cause a processor to execute or perform the program instructions. The media may also include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for supporting computer aided diagnosis (CAD), the apparatus comprising:
   a display;
   a memory configured to store instructions; and
   a processor, upon executing the stored instructions, configured to:
      determine a duration during which a remaining image of a first region of interest (ROI) detected from a first image frame is displayed; and
      control to the display to display a remaining image of a second ROI of a second image frame on the first image frame, in response to the first image frame being acquired within a duration predetermined to display the remaining image of the second ROI,
   wherein the first image frame is obtained subsequent to the second image frame.

2. The apparatus of claim 1, wherein the processor determines the duration of displaying the remaining image of the first ROI based on at least one of a predetermined duration of displaying the remaining image of the first ROI, reliability of a detection result of the first ROI, a size of the detected first ROI, and a movement speed of an image scanner used to acquire the first and second image frames.

3. The apparatus of claim 2, wherein the processor is further configured to determine the duration of displaying the remaining image of the first ROI in direct proportion to the reliability of the detection result of the first ROI.

4. The apparatus of claim 2, wherein the processor is further configured to determine the duration of displaying the remaining image of the first ROI in inverse proportion of the size of the detected first ROI.

5. The apparatus of claim 2, wherein the processor is further configured to determine the duration of displaying the remaining image of the first ROI to be a period that ends when the speed of the image scanner is below a predetermined threshold, or a moving direction of the image scanner is opposite to a previous moving direction.

6. The apparatus of claim 5, wherein the image scanner is a probe, and the apparatus further comprises a probe speed detector configured to detect the movement speed of the probe.

7. The apparatus of claim 1, wherein the processor is further configured to control the display to terminate, according to a user's instruction, the displaying the remaining image of the second image frame, which is displayed in the first image frame.

8. The apparatus of claim 1, wherein the processor is further configured to control the display to display, in the first image frame, the remaining image of the second ROI that is distinguished from the first ROI of the first image frame.

9. The apparatus of claim 1, wherein the processor is further configured to control the display to display, in the first image frame, the remaining image of the second ROI by using different colors, brightness, transparency, types of lines, or marking shapes, according to elapsed time.

10. The apparatus of claim 1, wherein the processor is further configured to control the display to display the remaining image of the second ROI at a position of the first image frame that is predicted based on a scanning path of an image scanner used to acquire the first and second image frames.

11. The apparatus of claim 1, wherein the processor is further configured to control the display to display at least one of results of ROIs detected up to a present time, diagnosis results of ROIs detected from the first image frame or detected up to the present time, locations of ROIs unrecognized by a user among regions of interest detected up to the present time, and guide information for redetecting an ROI unrecognized by the user.

12. The apparatus of claim 11, wherein the results of ROIs detected up to the present time comprise at least one of a total number of ROIs detected up to the present time; a number of ROIs that have been checked by the user among the ROIs detected up to the present time; and a number of ROIs that have not been checked by the user among the ROIs detected up to the present time.

13. The apparatus of claim 12, wherein the processor is further configured to determine whether a user checks the second ROI based on whether a movement speed of an image scanner used to acquire the second image frame is reduced below a predetermined threshold when detecting the second ROI, or based on whether a moving direction of the image scanner used when detecting the second ROI is changed to a previous moving direction.

14. The apparatus of claim 11, wherein the guide information comprises at least one of information about time elapsed since detection of an ROI unrecognized by the user, and information about moving directions of an image scanner for redetecting the ROI unrecognized by the user.

15. The apparatus of claim 1, wherein the processor is further configured to detect the first ROI from the first image frame.

16. A method of supporting computer aided diagnosis (CAD), the method comprising:
   determining a duration during which a remaining image of a first region of interest (ROI) detected from a first image frame is displayed;
   displaying a remaining image of a second ROI of a second image frame on the first image frame, in response to the first image frame being acquired within a duration predetermined to display the remaining image of the second ROI,
   wherein the first image frame is obtained subsequent to the second image frame.

17. The method of claim 16, wherein the determining the duration comprises determining the duration of displaying the remaining image of the first ROI based on at least one of a predetermined duration of displaying the remaining image of the first ROI, reliability of a detection result of the first ROI, a size of the detected first ROI, and a movement speed of an image scanner used to acquire the first and second image frames.

18. The method of claim 16, further comprising terminating, according to a user's instruction, displaying the remaining image of the second image frame, which is displayed in the first image frame.

19. The method of claim 16, wherein the displaying comprises displaying, in the first image frame, the remaining image of the second ROI by using different colors, brightness, transparency, types of lines, and marking shapes, according to elapsed time.

20. The method of claim 16, wherein the displaying comprises displaying at least one of results of ROIs detected up to a present time, diagnosis results of ROIs detected from the first image frame or detected up to the present time, locations of ROIs unrecognized by a user among ROIs detected up to the present time, and guide information for redetecting ROIs unrecognized by the user.

* * * * *